(12) United States Patent
Bzostek et al.

(10) Patent No.: US 8,534,293 B2
(45) Date of Patent: Sep. 17, 2013

(54) APPARATUS FOR ALIGNING NEEDLE WITH PORT OF INFUSION DEVICE

(75) Inventors: Andrew M. Bzostek, Erie, CO (US); Steven L. Hartmann, Superior, CO (US); Scott L. Kalpin, Harris, MN (US)

(73) Assignee: Medtronic, Inc, Minneapolis, MN (US)

( * ) Notice: Subject to any disclaimer, the term of this patent is extended or adjusted under 35 U.S.C. 154(b) by 1098 days.

(21) Appl. No.: 12/207,566

(22) Filed: Sep. 10, 2008

(65) Prior Publication Data

US 2009/0227863 A1    Sep. 10, 2009

Related U.S. Application Data

(60) Provisional application No. 60/973,824, filed on Sep. 20, 2007.

(51) Int. Cl.
*A61B 19/00* (2006.01)
*A61B 5/05* (2006.01)

(52) U.S. Cl.
USPC ...... 128/899; 600/424; 604/288.01; 604/116; 604/175; 604/288.04; 128/897; 128/898

(58) Field of Classification Search
USPC ............. 128/897–899; 600/424; 604/116, 604/175, 288.01–288.04
See application file for complete search history.

(56) References Cited

U.S. PATENT DOCUMENTS

| | | | |
|---|---|---|---|
| 5,171,228 A | 12/1992 | McDonald | |
| 5,375,596 A | 12/1994 | Twiss | |
| 5,617,857 A | 4/1997 | Chader | |
| 6,009,878 A | 1/2000 | Weijand | |
| 6,021,343 A | 2/2000 | Foley | |
| 6,305,381 B1 | 10/2001 | Weijand | |
| 6,332,089 B1 | 12/2001 | Acker | |
| 2004/0199220 A1 | 10/2004 | Cantlon | |
| 2006/0211914 A1* | 9/2006 | Hassler et al. | 600/37 |
| 2006/0278247 A1 | 12/2006 | Hunter | |

FOREIGN PATENT DOCUMENTS

| | | |
|---|---|---|
| EP | 0 723 783 | 7/1996 |
| EP | 1 832 254 | 9/2007 |
| WO | WO 98/00060 | 1/1998 |
| WO | WO 2006/031490 | 3/2006 |

OTHER PUBLICATIONS

PCT Search Report dated Dec. 22, 2008.

\* cited by examiner

*Primary Examiner* — Christine Matthews
*Assistant Examiner* — Sunita Reddy
(74) *Attorney, Agent, or Firm* — Mueting Raasch & Gebhardt PA

(57) ABSTRACT

A needle apparatus for aligning a needle with a port of an implantable infusion device includes a needle anchoring portion configured to axially fix the apparatus relative to a needle to be inserted into the port. The needle apparatus further includes a port locating portion fixable relative to the needle anchoring portion. The port locating portion includes a port location signal receiver module for receiving a signal from an implantable infusion device regarding the location of the port of the infusion device.

13 Claims, 12 Drawing Sheets

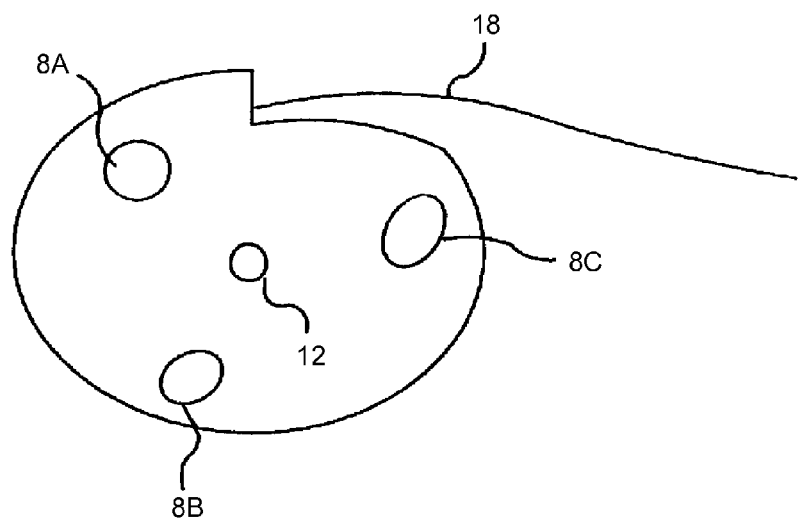
FIG. 2C
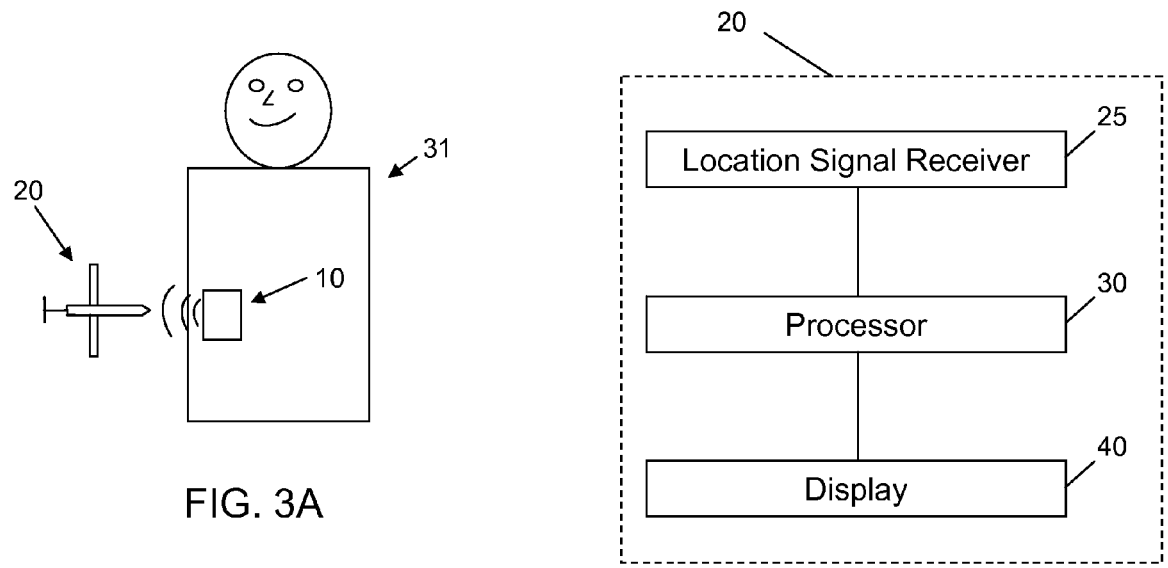
FIG. 3A
FIG. 4A

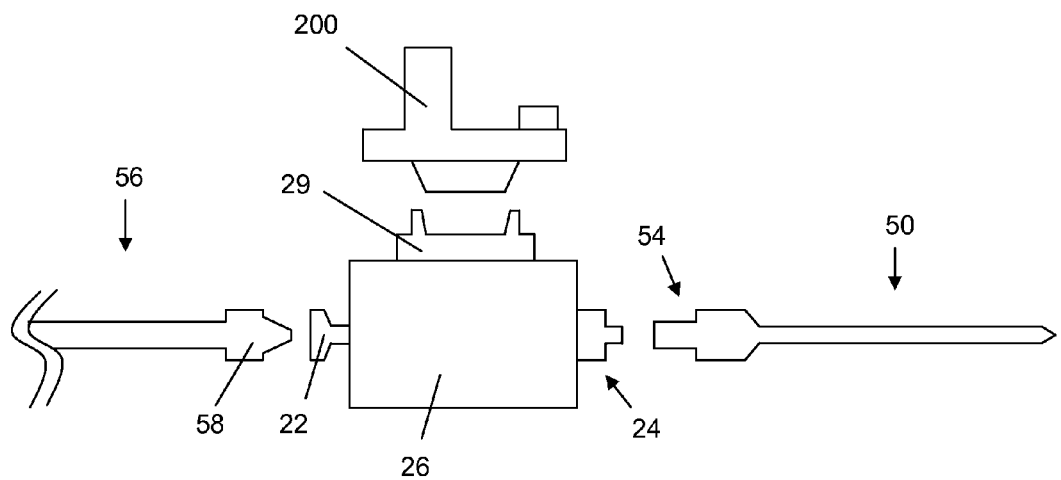
FIG. 8
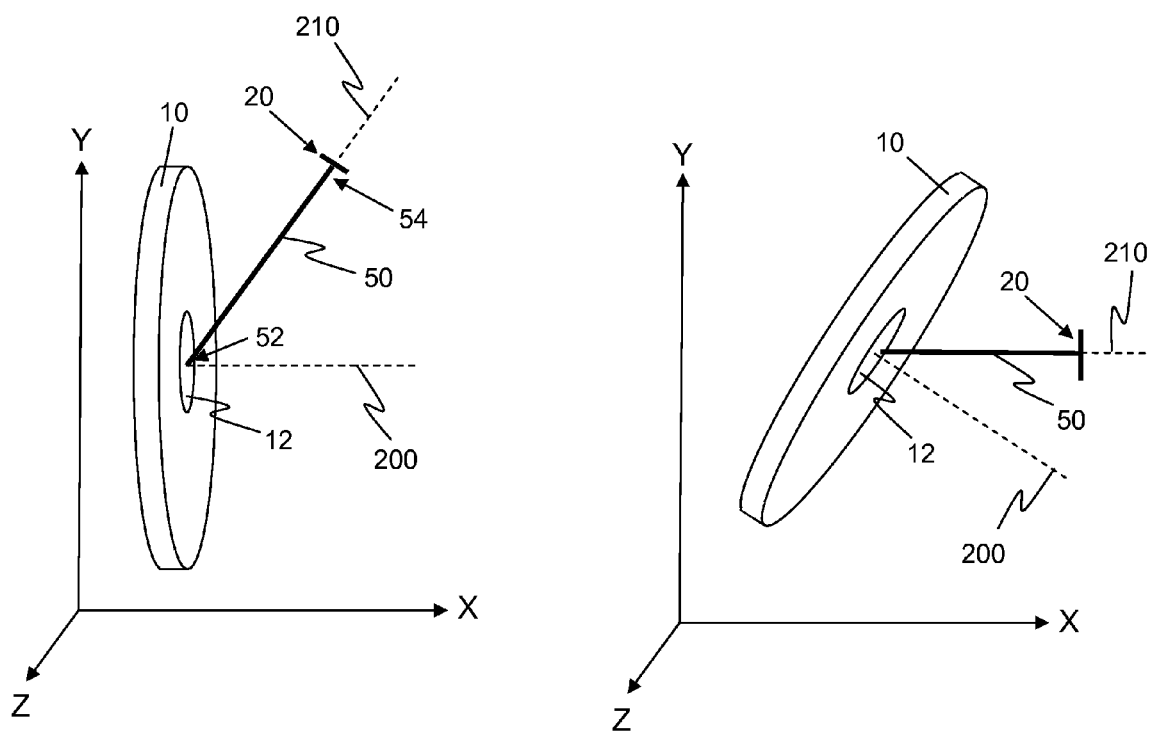
FIG. 9A
FIG. 9B

APPARATUS FOR ALIGNING NEEDLE WITH PORT OF INFUSION DEVICE

RELATED APPLICATION

This application claims the benefit of U.S. Provisional Application No. 60/973,824, filed Sep. 20, 2007.

FIELD

This disclosure relates, inter alia, to implantable infusion devices, and more particularly to devices, systems and methods for percutaneously inserting needles in implanted infusion devices.

BACKGROUND

Implantable infusion devices, which can deliver low levels of therapeutic agents to target locations in patients, have been employed or contemplated for treating a variety of diseases. Such implantable infusion devices are often permanently implanted and may be used to periodically or continuously deliver the therapeutic agent. To ensure continued delivery of the therapeutic agent to the patient over time, reservoirs of such devices need to be replenished. Typically such replenishment is accomplished by inserting a needle though the patient's skin and through a septum covering a port in fluid communication with the reservoir.

Because such a device is implanted and thus not able to be directly seen, care must be taken to ensure that the needle is properly placed into the device before injection. If the needle misses the device and, in particular, misses the drug reservoir in the device, the drugs will be immediately dispensed in the body, having potentially dire consequences for the patient. Moreover, if the needle is not fully placed through the septum and into the drug reservoir, the drug reservoir will not be adequately filled, also having potentially dire consequences for the patient.

Port locator devices have previously been described. Such devices are intended to be placed on the patient's skin adjacent the implanted infusion device. A hole or opening in the port locator is positioned over the reservoir port. A needle may then be inserted through the hole in the port locator, through the patient's skin, and into the reservoir port. However, such port locator devices, even when simplistically designed, are difficult to use.

For example, a physician typically uses one hand to identify by touch the location of the implanted device and steady the orientation of the device and uses the other hand to place the port locator in position relative to the implanted device. Thus the physician has no hand available to insert the refill needle through the port locator and into the reservoir port of the implanted device. While it is possible to perform the refill procedure with such port locator devices, the use of such devices is often awkward and may result in inaccurate needle placement due to the awkwardness.

BRIEF SUMMARY

The present disclosure presents methods, systems, and devices that allow for accurate placement of a needle into a port of an implanted infusion device in an easy to use manner. The methods, systems and devices include axially fixing a port locating portion relative to the needle. Thus, the port locating device and the needle may be managed with a single hand, leaving a hand available for palpating the patient in the region of the implanted device.

In an embodiment, a needle apparatus for aligning a needle with a port of an implantable infusion device is described. The needle apparatus includes a needle anchoring portion configured to axially fix the apparatus relative to the needle. The needle apparatus further includes a port locating portion fixable relative to the needle anchoring portion. The port locating portion includes a port location signal receiver module for receiving a signal from an implantable infusion device regarding the location of the port of the infusion device.

In an embodiment, a needle apparatus for aligning a needle with a port of an implantable infusion device is described. The needle apparatus includes a needle anchoring portion configured to axially fix the apparatus relative to the needle. The needle anchoring portion has a proximal end portion, a distal end portion, and a lumen extending through the needle anchoring portion from the proximal end portion to the distal end portion, and is configured such that, when axially fixed relative to the needle, the lumen of the needle anchoring portion is in fluid communication with a lumen of the needle. The needle apparatus further includes a port locating portion fixable relative to the needle anchoring portion. The port locating portion includes a port location signal receiver module for receiving a signal from an implantable infusion device regarding the location of the port of the infusion device.

In an embodiment, a needle apparatus for aligning a needle with a port of an implantable infusion device is described. The needle apparatus includes a needle anchoring portion configured to axially fix the apparatus relative to a needle. The apparatus further includes a port locating portion fixed relative to the needle anchoring portion. The port locating portion includes a port location signal receiver module for receiving a signal from the infusion device regarding the location of the port. The apparatus also includes a display configured to provide a user of the apparatus information regarding the orientation of the needle relative to the port based on the signal from the infusion device received by the tracking antenna module.

In an embodiment, a needle apparatus for aligning a needle with a port of an implantable infusion device is described. The needle apparatus includes a needle anchoring portion configured to axially fix the apparatus relative to a needle to be inserted into the port. The needle apparatus further includes a port locating portion fixable relative to the needle anchoring portion. The port locating portion includes a port location signal receiver module for receiving a signal from an implantable infusion device regarding the location of the port of the infusion device.

In an embodiment, a method is described for locating a port of an implantable infusion device into which a needle is to be inserted. The method includes sensing a signal from the implantable infusion device regarding the location of the port. The signal is sensed at a fixed axial location relative to a needle to be inserted into the port. The method further includes displaying information regarding the orientation of the needle relative to the port based on the sensed signal.

By providing devices, systems and methods that axially fix a port locating portion relative to a needle, more accurate placement of the needle in a port of an implanted infusion device should result. This and other advantages will be readily understood from the following detailed descriptions when read in conjunction with the accompanying drawings.

BRIEF DESCRIPTION OF THE DRAWINGS

FIGS. 2B-C are schematic diagrams of a top views of a representative implantable infusion devices.

FIGS. 3A-C are schematic diagrams of a representative systems in the environment of a patient.

FIGS. 4A-C are schematic block diagrams showing some components of representative systems.

FIG. 8 is a schematic side view of representative components of a needle apparatus system.

FIGS. 9A-B are schematic perspective views of representative implantable infusion devices.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The present disclosure describes, inter alia, methods, systems and devices that employ a port locating portion axially fixed relative to a needle, allowing for more accurate placement of the needle in a port of an implanted infusion device. Improved accuracy should result due to the ability to manage the port locating portion and the needle with a single hand.

The teachings of the present disclosure may be applied to any implantable infusion device having a port. The infusion device may be an active or passive infusion device. For example, the infusion device may contain a peristaltic pumping mechanism, a piston pump, an osmotic pump, or the like. The infusion device may be programmable, such as Medtronic's SYNCHROMED II infusion device.

Figure 1A:
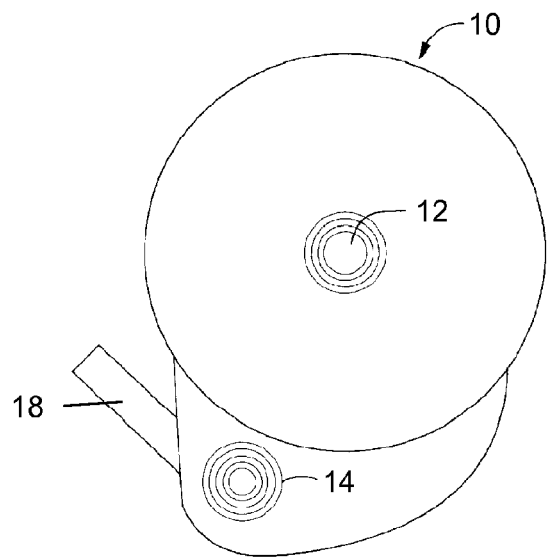
FIG. 1A is a schematic diagram of a top view of a representative implantable infusion device.
Figure 1B:
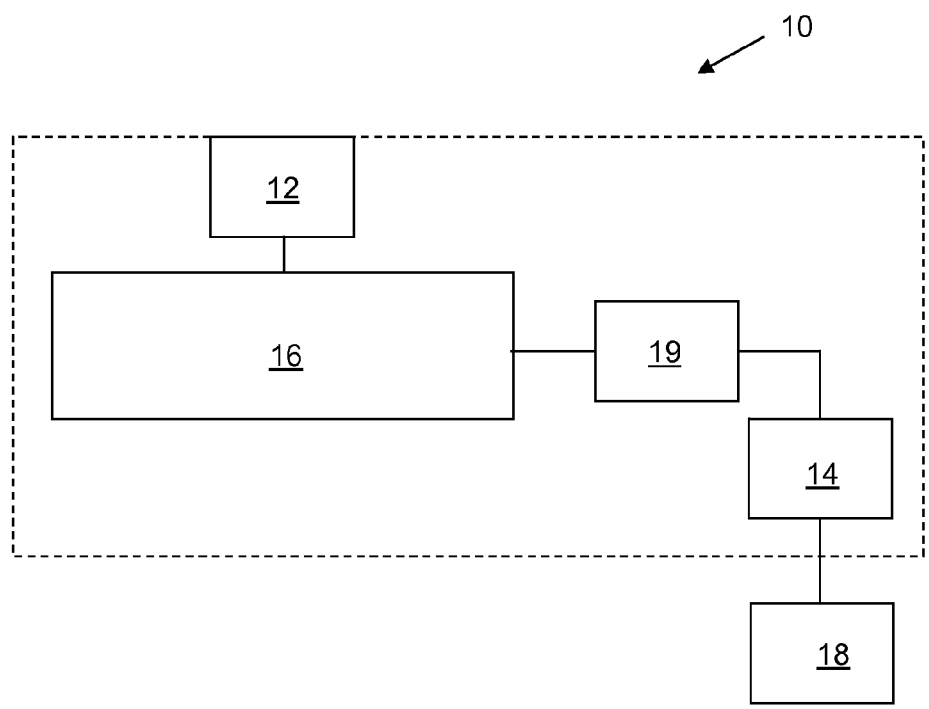
FIG. 1B is a schematic block diagram showing some components in a fluid flow path of a representative implantable infusion device.

Referring to FIGS. 1A-B, schematic diagrams of representative infusion devices 10 are shown. As shown in the top view of FIG. 1A, infusion device 10 may include a refill port 12 and a catheter access port 14. The refill port 12 is in fluid communication with reservoir 16 and allows entry of a needle for insertion or withdrawal of fluid to or from reservoir 16. Fluid flows from reservoir 16 to outlet catheter 18 to a desired location of a patient. In infusions devices 10 including both a refill port 12 and a catheter access port 14, catheter access port 14 is typically located downstream of reservoir 16 from refill port 12. Catheter access port allows for withdrawal of fluid from catheter 18 or insertion of fluid, such as a bolus drug delivery, into catheter 18. A one-way valve 19 may be positioned between reservoir 16 and catheter access port 14 to prevent withdrawal of fluid from reservoir 16 or infusion of fluid into reservoir 16 when fluid is withdrawn or infused into catheter access port 14.

Figure 2A:
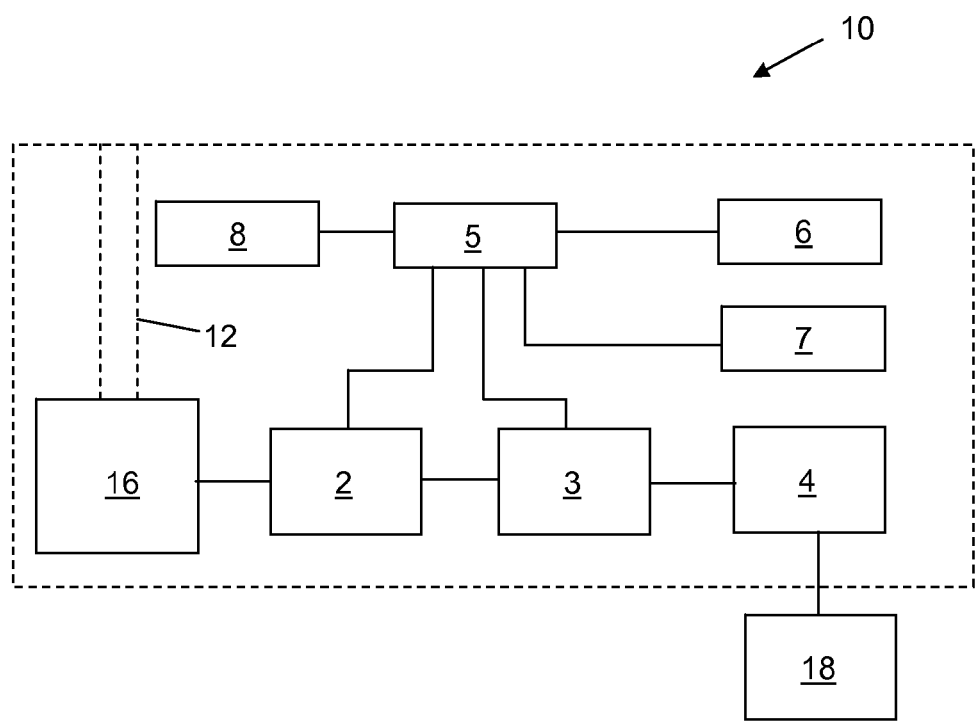
FIG. 2A is a schematic block diagram showing some components of a representative implantable infusion device.

Locating mechanisms and devices, as described in more detail below, may be employed with regard to any port of an implantable infusion device 10. However for the sake of clarity and convenience, locating mechanisms will be described herein with regard to refill port 12. Referring to FIG. 2A, a block diagram of an embodiment of an infusion device 10 capable of generating a signal regarding the location of the refill port 12 is shown. In the depicted embodiment, a safety valve 2 is located between reservoir 16 and pump 3, and a flow restrictor 4 is located between pump 3 and catheter 18. However, it will be understood that any suitable fluid pathway and associated components may be employed with the teachings herein. Safety valve 2 and pump 3, in the depicted embodiment, are operably coupled to electronics 5. Electronics 5 can control the operation of, and provide power to (as appropriate), valve 2 and pump 3. Electronics 5 are operably coupled to power source 6 and to telemetry module 7 in the depicted embodiment. Telemetry module 7 provides for communication between implantable device 10 and an external device, such as a programmer. While module 7 is referred to herein as "telemetry" module, it will be understood that other forms of wireless communication may readily be substituted where appropriate for telemetry. Examples of forms of wireless communication include Bluetooth®, 802.11, and Medical Implant Communication Service (MICS) frequency band communication.

Electronics 5 are further operably coupled to, and may control operation of and provide power to, port location signaling module 8. Port location signaling module 8 may include any suitable components capable of generating a signal detectable by an external device. The external device, or a device operably coupled to the external device, may derive the location of the port 12 based on the signal. For example, port location signaling module may include components described in U.S. Pat. No. 6,305,381, entitled "System for locating implantable medical device", issued on Oct. 23, 2001, which patent is hereby incorporated herein by reference to the extent that it does not conflict with the disclosure presented herein.

Figure 2B:
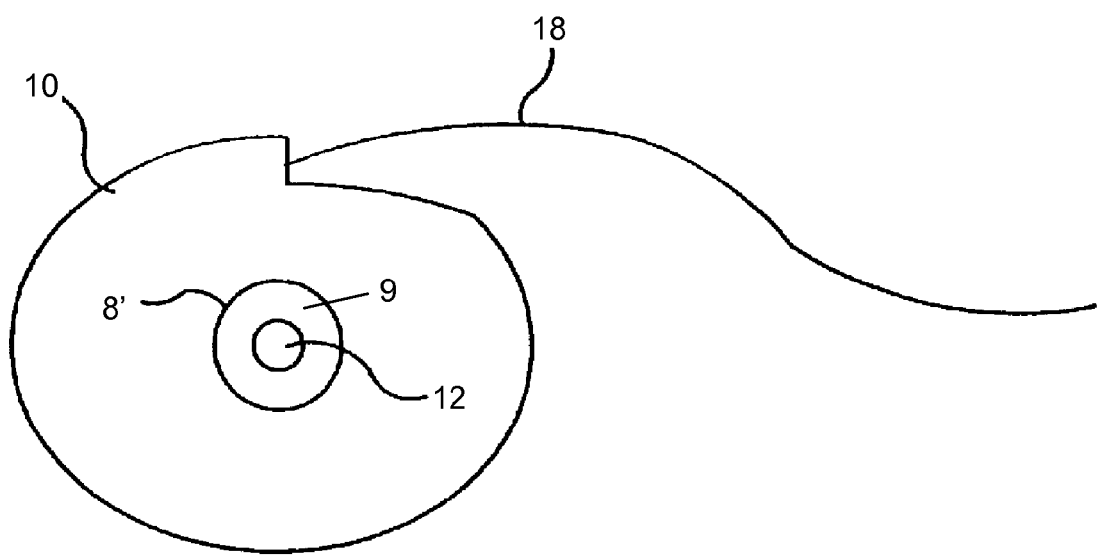

Referring to FIG. 2B, port location signaling module may include a coil 8' having an opening 9 coaxially aligned with port 12. Although port locating signaling module 8 is shown in FIG. 2A as a separate module, it should be appreciated that coil 8' may be fashioned by using a telemetry or recharge coil of the device 10. In the embodiment depicted in FIG. 2C, port location signaling module includes a plurality of coils 8A, 8B, and 8C. Such a plurality of coils 8A, 8B, 8C may be used to each emit at a differing frequencies, or other suitable parameter, so that the external device may accurately sense the location of the port 12 in addition to the proper orientation of the external device relative to the implantable infusion device 10, which is discussed in more detail below.

Figure 3B:
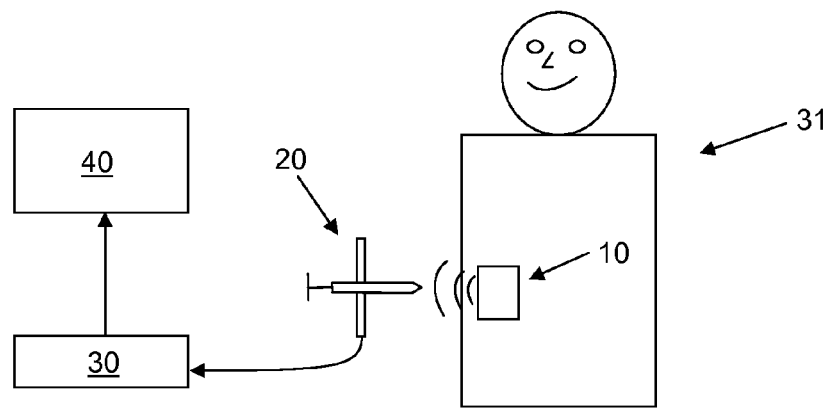
Figure 4B:
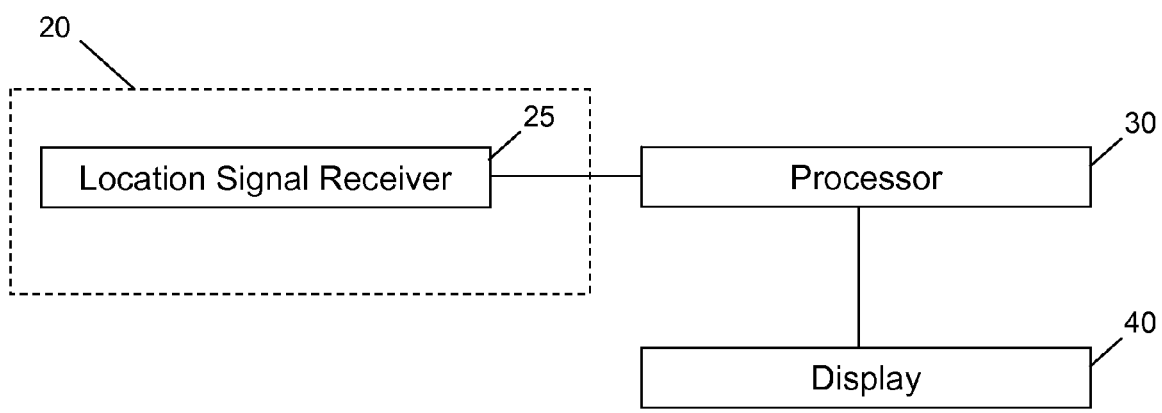
Figure 3C:
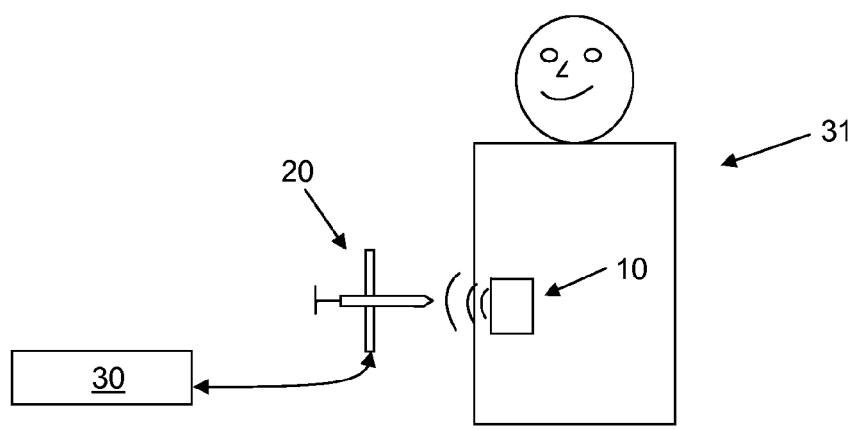
Figure 4C:
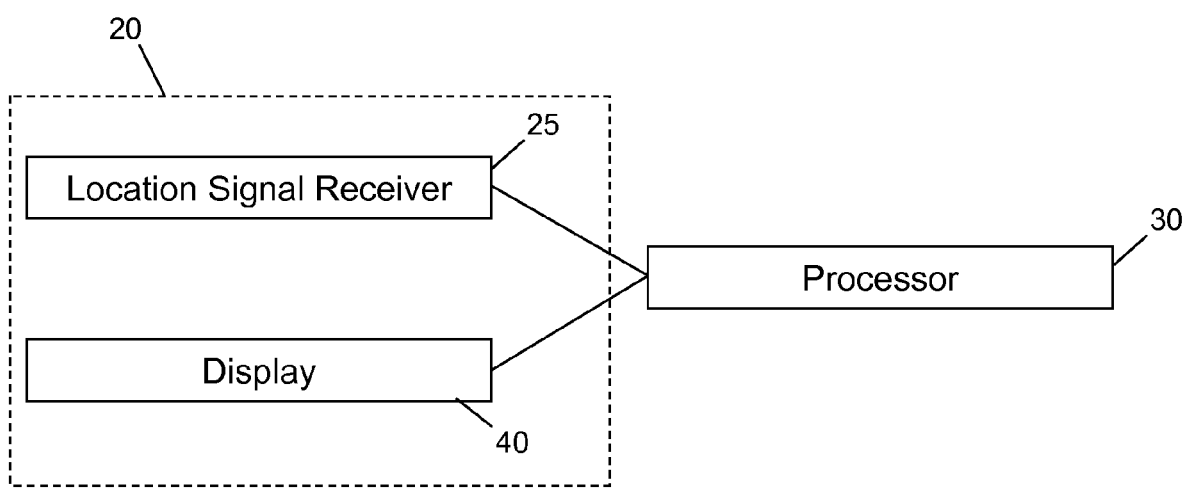

Referring now to FIGS. 3A-C, an implanted infusion device 10, via port location signaling module, emits signal through the skin of a patient 31. An external needle apparatus 20 detects signal from implanted device 10 and determines location or location and orientation of the implanted port, allowing for accurate infusion or withdrawal of fluid from implanted infusion device 10. Needle apparatus 20 may be self-contained, i.e., apparatus 20 may contain all components necessary or desired for proper location or alignment of apparatus 20 with the port of implanted device 10, or may be operably coupled (e.g., wirelessly or via wires) to additional components that may facilitate location of, and alignment with, a port of the implanted device 10. Such components include a location signal receiver module 25, a processor 30 for determining the relative location or alignment of the needle apparatus 20 to the port of the implanted device 10, and a display 40 for providing a user of the needle apparatus with an indication of the relative location and alignment of needle apparatus 20 and port of implanted device 10 (see, e.g., FIGS. 4A-C).

Location signal receiver module 25 is contained within or about needle apparatus 20 or a portion thereof and contains one or more components for detecting the signal transmitted from the port locating signal module of the implanted device 10. It will be understood that components of location signal receiver module will vary according to the type of signal transmitted from the implanted device 10. By way of example, and referring to FIG. 5A, location signal receiving module of needle apparatus 20 may include a plurality of sensing arrays 26-A, 26-B, 26-C, 27-A, 27-B, 27-C, 28-A, 28-B, 28-C of antennas, each series attuned to sense the output of a corresponding coil 8A, 8B, 8C (see, e.g. FIG. 2C) of port location signaling module of implantable infusion device 10.

Figure 5A:
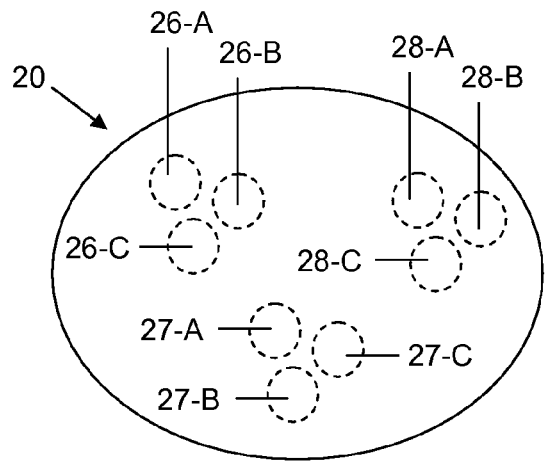
FIG. 5A is a diagrammatic illustration of a schematic view of a representative needle apparatus.
Figure 5B:
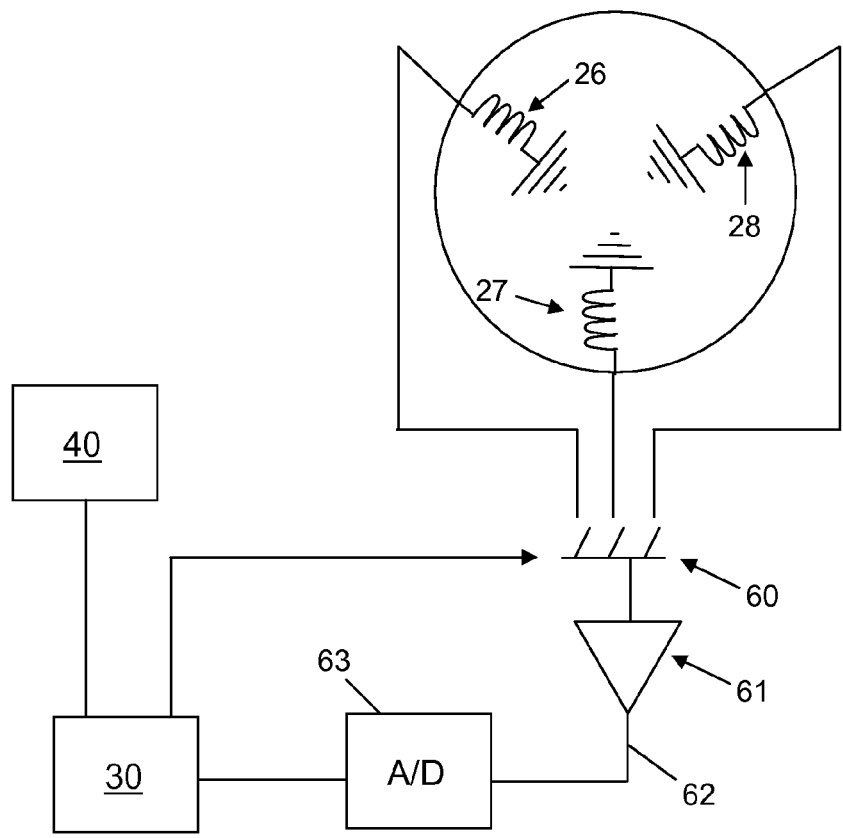
FIG. 5B is a schematic circuit and block diagram that may be used in conjunction with the needle apparatus depicted in FIG. 5A.

FIG. 5B depicts an embodiment of a circuit that may be used with a needle apparatus 20 depicted in FIG. 5A. As seen, antennas 26, 27 and 28 of the location signal receiver module are coupled to processor 30 through switch 60. Through such a coupling this embodiment uses a sampling technique to alternatingly sample the signal on each antenna. Each such sampled signal is then passed through amplifier 61 which also provides a filtering function and outputs the signal on line 62 as an RSSI. The signal is then processed through analog digital converter 63 where it is then put into the processor 30. Processor 30 compares each of the signals sampled from the antennas. Processor 30 may then determine whether the same amount of energy is being sensed by each antenna, which, due to the geometry of implant coils 8A, 8B, 8C and the antennas 26, 27, 28 of the needle apparatus 20, indicates alignment, in this case both X,Y alignment and angle alignment, of the needle of the needle apparatus 20 and the port of the implantable infusion device 10. Processor 30 may be operably coupled to a display 40 and cause a visual representation of the relative angular alignment or position of needle of needle apparatus 20 and port of infusion device 10 to be displayed, allowing user to adjust the position of needle apparatus accordingly. In an alternate embodiment, the system uses a technique in which each coil is oppositely coupled, that is in anti-phase, such that when a null is sensed the coils are each sensing an equal amount of energy, rather than using a sampling technique to detect the energy sensed by each antenna (see, e.g., U.S. Pat. No. 6,305,381 for more detail).

Of course, any suitable sensing combination of port locating signaling module of infusion device and location signal receiver module of needle apparatus may be employed. In various embodiments, the sensing combination is capable of providing information regarding X,Y alignment of the needle and the port. In various embodiments, the sensing combination is capable of providing information regarding the X,Y alignment of, and the angle of orientation between, the needle and the port. The sensing combination may also provide information regarding the distance from the tip of the needle to the port.

Referring back to FIGS. 3A-C and 4A-C, needle apparatus 20 may be a self contained system and may include location signal receiver module 25, processor 30, and display 40 (see FIGS. 3A and 4A). Alternative configurations are also possible, where one or more system components are external to needle apparatus 20. For example, and referring to FIGS. 3B-C and 4B-C, location signal receiver module 25 disposed in, on or about needle apparatus 20 may send information, either via cables or wirelessly, to processor 30. Based on the received information, processor 30 may then determine the relative orientation of needle of needle apparatus 20 and port of infusion device 10. Information regarding the relative positions of the needle of needle apparatus 20 and the port of infusion device 10 may then be displayed on display 40. In the embodiments depicted in FIGS. 3B and 4B, display 40 is external to needle apparatus 20. In the embodiments depicted in FIGS. 3C and 4C, display 40 is a component of the needle apparatus 20.

Figure 6A:
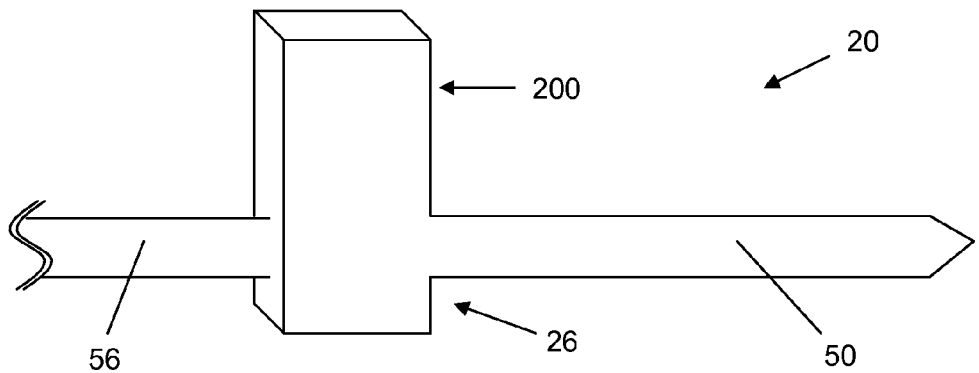
FIGS. 6A-C are schematic perspective diagrams of representative needle apparatuses.
Figure 6B:
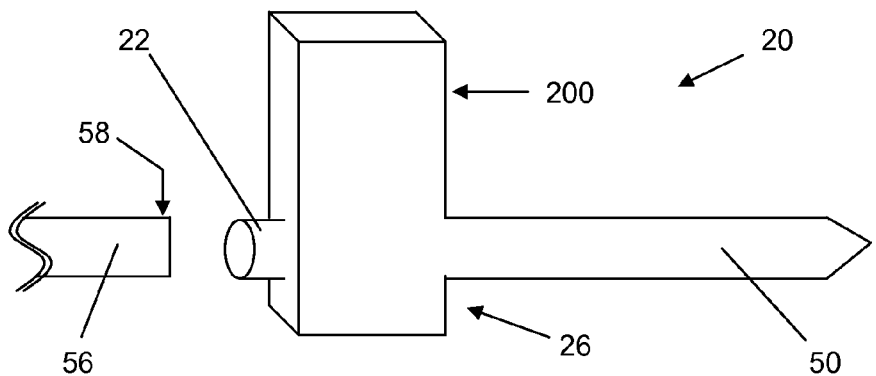
Figure 6C:
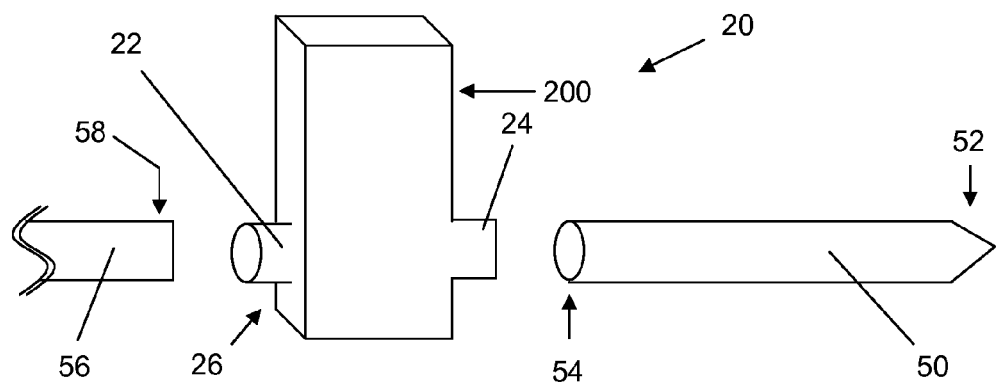

Referring now to FIGS. 6A-C, perspective views of representative needle apparatuses are shown. Needle apparatus 20 includes a needle anchoring portion 26 configured to axially fix the needle apparatus 20 relative to the needle 50. Needle apparatus 20 also includes a port locating portion 200 fixable relative to the needle anchoring portion 26. It will be understood that, as used herein, "fixable" and the like includes permanently affixed, detachable fixable and the like. Port locating portion 200 houses location signal receiver module 25 (see, e.g. FIGS. 4A-C) and may include processor 30, display 40 and any other necessary or desirable electronics, such as a power supply, digitizing electronics, or the like. Of course, as discussed above (e.g., with regard to FIGS. 4A and C), processor 30 or display 40 may be housed external to port locating portion 200 of needle apparatus 20. In the embodiment depicted in FIG. 6A, needle apparatus 20 includes needle 50 and tubing 56 or syringe or the like. In the embodiment shown in FIG. 6B, needle apparatus 20 includes needle 50 and includes a distal end portion 22 configured to fluidly couple to proximal end portion 58 of tubing 56 or syringe or the like. In the embodiment depicted in FIG. 6C, needle apparatus 20 serves as an adaptor configured to operably couple needle 50 to tubing 56 or syringe or the like. Needle apparatus 20 includes a proximal end portion 24 configured to axially fix needle anchoring portion 26 to proximal portion 54 of needle 50. Any suitable mechanism or connector may be used to axially fix needle anchoring portion 26 to needle 50.

Figure 7A:
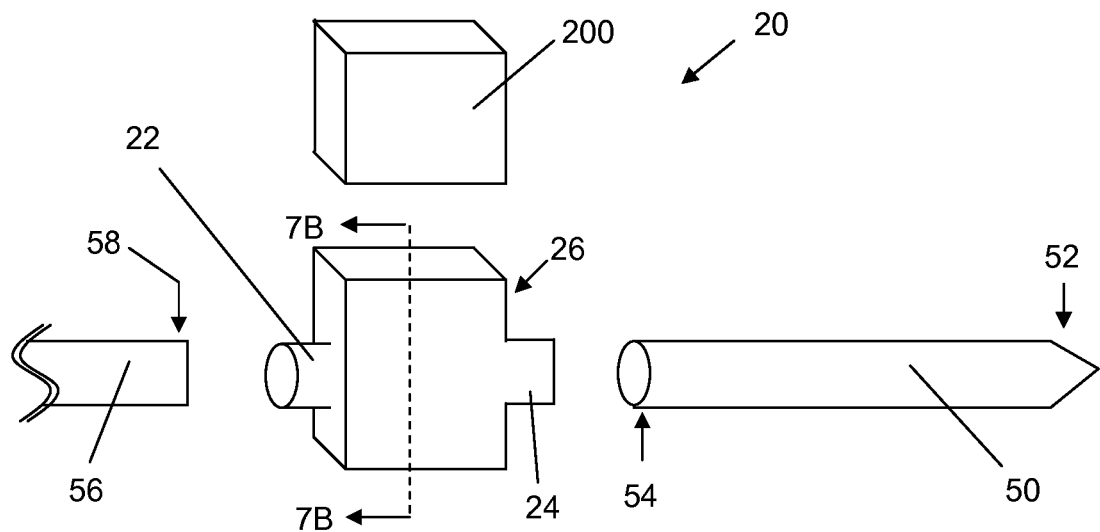
FIG. 7A is a schematic perspective diagram of a representative needle apparatus.

Referring to FIG. 7A, needle apparatus 20 may include a detachable port locating portion 200. Port locating portion 200 may be detachable in any manner, so long as it is fixable relative to needle anchoring portion 26 when in use. Having port locating portion 200 be detachable may be desirable, as needle anchoring portion 26 can be manufactured with little or no electronic components and be disposable. Removable port locating portion 200 which contains electronics (at least location signal receiver component electronics) may then be reusable.

Figure 7B:
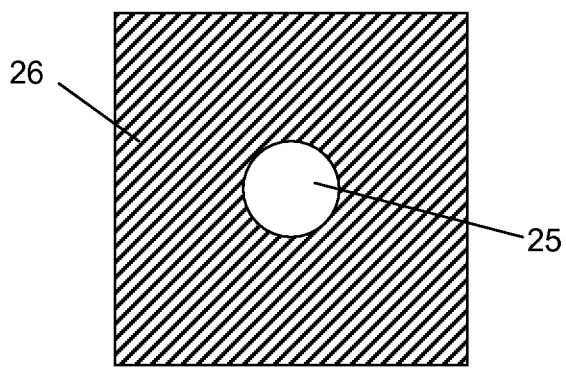
FIG. 7B is a schematic cross section taken along the line 7B-7B of the needle apparatus depicted in FIG. 7A.
Figure 10A:
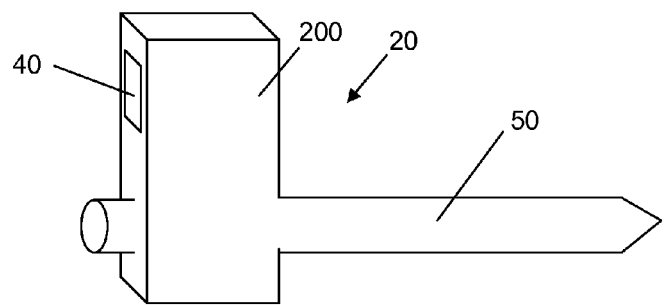
FIG. 10A is a schematic perspective diagram of a representative needle apparatus having a display.
Figure 10B:
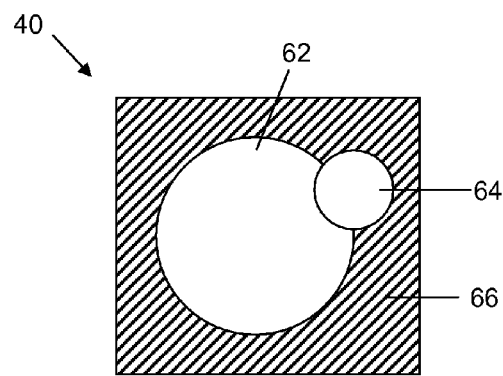
FIGS. 10B-D are schematic diagrams of representative user interfaces that may be displayed regarding the orientation of a needle relative to a port of an implantable infusion device.
Figure 10C:
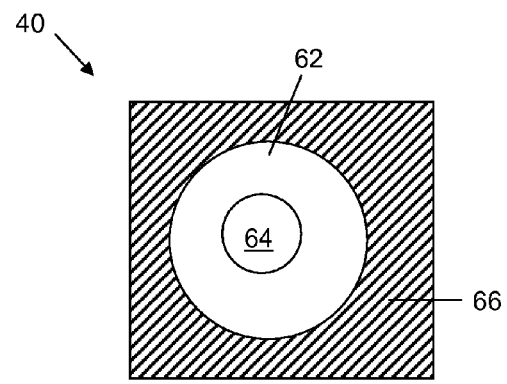
Figure 10D:
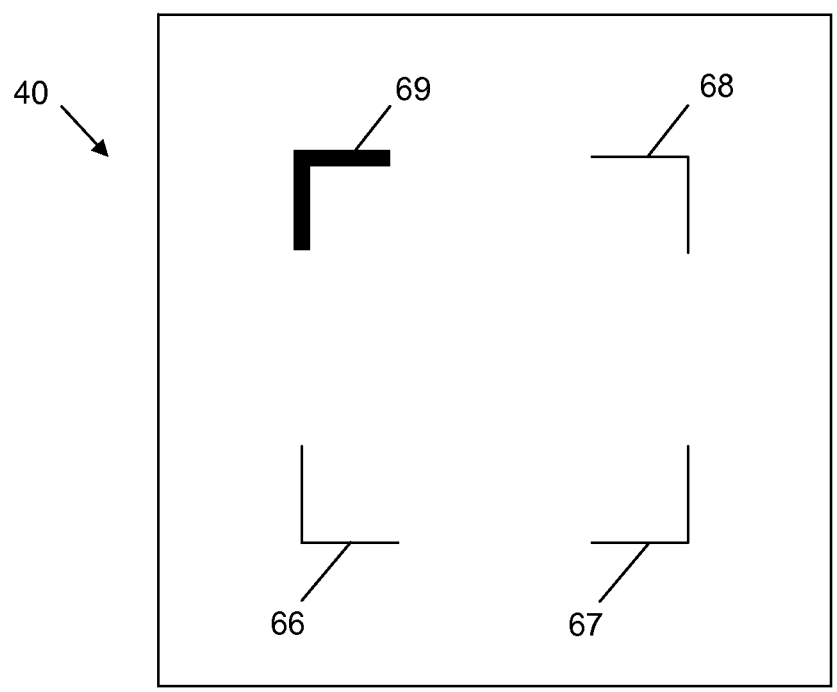

In the embodiment depicted in FIG. 7A, needle anchoring portion 26 has a proximal end portion 24, a distal end portion 22, and a lumen 25 (see, FIG. 7B, which shows a cross section through line 7B-7B of FIG. 7A) extending through the needle anchoring element from the proximal end portion 24 to the distal end portion 22. The lumen 25 is configured to be fluidly coupled with a lumen of the needle 50 and a lumen of the tubing 56 or syringe or the like. Of course needle anchoring portion 26 need not contain a lumen 25 configured to be fluidly coupled with the lumen to the needle 50 and may be axially fixed about an exterior surface of the needle 50 or otherwise axially fixed relative to needle 50.

Any suitable mechanism for axially fixing needle anchoring portion 26 relative to needle 50 may be employed. By way of example, and referring to the embodiment depicted in FIG. 8, luer connections may be used to axially secure needle anchoring portion 26 relative to needle 50. Proximal end portion 24 of needle anchoring portion 26 may contain a male luer connector, and distal end portion 54 of needle 50 may include a female luer connector. In the depicted embodiments, distal end portion 22 of needle anchor portion 26 also includes a female luer lock connector, and proximal end portion 58 of tubing 56, syringe, or the like may contain a male luer connection. The needle anchoring portion 26 depicted in the embodiment of FIG. 8 includes a mount 29, such as a snap on mount, for fixably and detachable receiving port locating portion 200. Of course, any suitable mechanism for detachably fixing port locating portion 200 relative to needle anchoring portion 26 may be used.

Referring now to FIGS. 9A-B, perspective views of implantable infusion devices are shown and illustrate the importance of alignment of a needle 50 with a port 12. In the figures, a desired alignment axis 200 of the port 12 is depicted and actual needle axis 210 of needle 50 is shown to be out of alignment with desired axis 200. If needle 50 is out of alignment, even though the proximal tip 52 of needle 50 is properly located as shown, injection or fluid withdrawal error may occur. Accordingly, proper alignment of actual needle axis 210 and desired needle axis 200 is important. As infusion device 10 is subcutaneously implanted and cannot be seen during procedures where needle 50 is to be inserted into port 12, a suitable mechanism for determining alignment of needle 50 with port 12 is desired.

In various embodiments, needle apparatus 20 may include a display 40 for indicating the relative position or orientation of needle 50 relative to a port of an implantable infusion device. One such embodiment is depicted in FIG. 10, where display 40 is disposed on or exposed through an external surface of port locating portion 200. Any suitable display 40, such as a LCD display, a series of LEDs, or the like, may be used. Any suitable user interface may be employed, such as a user interface described in Provisional Patent Application Ser. No. 60/973,827, entitled "Needle to Port Trajectory Indicator", filed on Sep. 20, 2007, to which U.S. patent application Ser. No. 12/207,093 filed on Sep. 9, 2008 and published on Mar. 26, 2009 as US 2009/0082782 claims priority, which provisional patent application is hereby incorporated herein by reference to the extent that it does not conflict with the present disclosure. For example, and referring to FIGS. 10B-C, indicators 62, 64 of the relative angular orientations of the target port of the infusion device (shown as indicator 62) and the needle (shown as indicator 64) may be shown on display 40. In the depicted embodiment, if needle orientation indicator 64 falls within or overlaps with the shaded area 66 (see, e.g., FIG. 10B), the trajectory of the needle is not aligned with the orientation of the port. A user of the needle apparatus may adjust the orientation of the apparatus until the needle position indicator 64 falls completely within the port position indicator region 62, indicating alignment of the needle with the port (see, e.g., FIG. 10C). By way of further example, and referring to FIG. 10D, X,Y position indicators 66-69 of the relative X,Y positions of the target port of the infusion device and the tip of the needle may be shown on display 40. In the depicted embodiment, X,Y position indicator 69 is thickened, brightened, turned on or the like relative to X,Y position indicators 66-68. A user of the needle apparatus may move the needle in the position indicated by X,Y position indicator 69 to positionally align the needle with the port. Of course a combination of angular and positional alignment may be employed for enhanced accuracy. For example, display 40 may depict both angular orientation indicators 62, 64 and X,Y position indicators 66-68. Once aligned, the needle may then be advanced through the patient's skin and into the targeted port of the infusion device.

For the processor to accurately calculate the orientation and relative position of the needle to the targeted port and cause display 40 to render an accurate image of the relative position and orientation, the relative position of the port location signal receiver 25 to the needle 50 should be taken into account. For example, and referring back to FIGS. 6A-C, port locating portion 200 houses the port location signal receiver 25. In the embodiments, depicted in to FIGS. 6A-C, the port locating portion 200 is off center from needle 50. Accordingly, the position of the port location signal receiver 25 is off center from the needle. Information regarding the distance from axial center of the needle 50 and the distance along the length of the needle from the tip 52 to the port locating portion 200 may be accounted for in making a determination of the relative positions of needle 50 and the target port.

It will be understood that the components and devices described in FIGS. 1-9 are but examples of components and devices that may be employed to detect relative orientation of a needle and a targeted port and that many other device or system configurations may be employed to carry out the methods described below. However, for the sake of convenience, the discussion that follows with regard to the method illustrated in the flow diagram of FIG. 11 will refer to components as described with regard to FIGS. 1-9.

Figure 11:
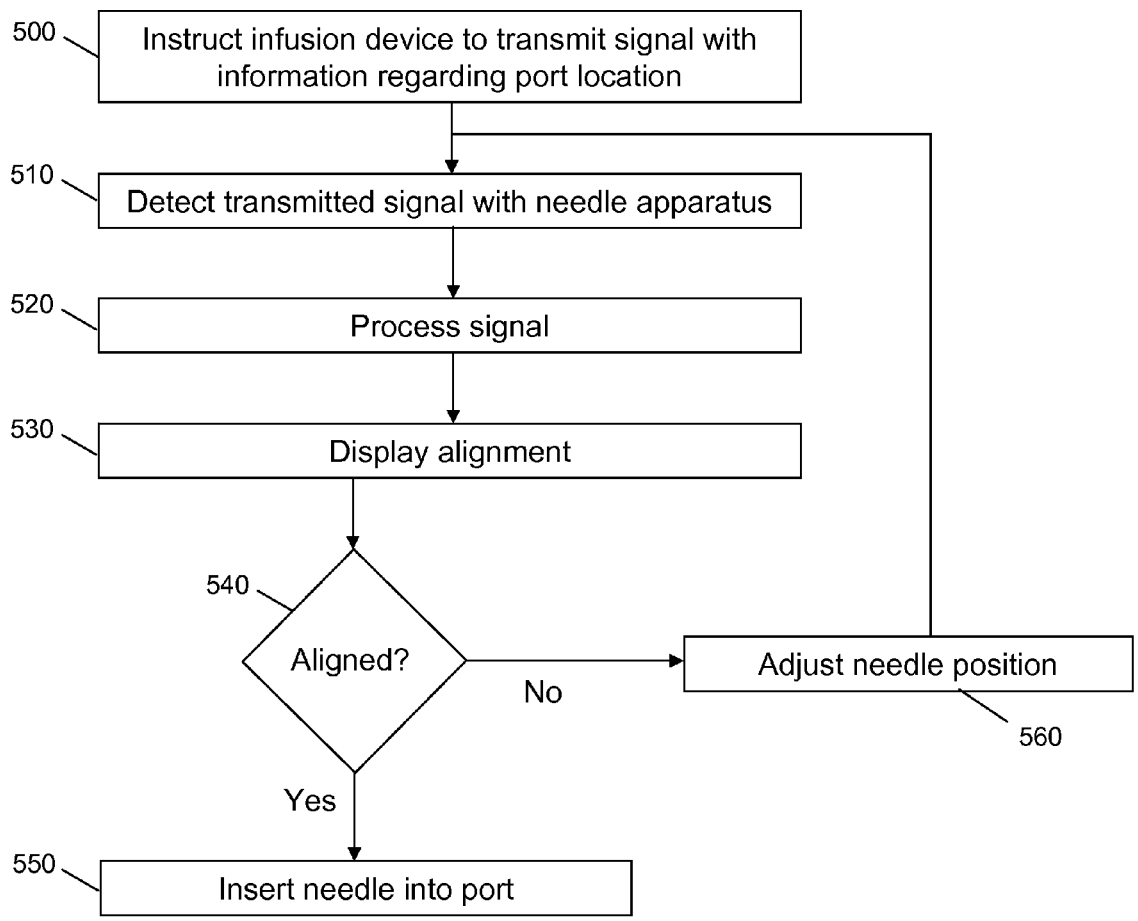
FIG. 11 is a flow diagram of a representative method.

Referring to FIG. 11, a flow diagram of a representative method is shown. According to various embodiments, a method includes instructing an implantable infusion device 10 to transmit a signal, e.g. via location module 8, with information regarding location of a target port 12 (500). The instructions to transmit the signal may be provided to the infusion device 10 from an external device, such as a programmer, that is in communication with a telemetry module 7 of the infusion device 10. The transmitted signal may then be detected via port location signal receiver 25 of a needle apparatus (510). Processor 30 may receive information from port location signal receiver 25 to determine the relative alignment of the needle 50 and the targeted port 12 (520). The processor 30 may cause a display 40 to show the relative alignment of the needle 50 and the targeted port 12 via indicators 64, 62 (530). A user of the needle apparatus 20, by viewing display 40, may determine whether the needle 50 and the targeted port 12 are aligned (540). If aligned, the user may insert the needle 50 into the port 12 (550). If the needle 50 and port 12 are not aligned, the position or orientation of the needle 50 may be adjusted by the user (560). Steps 510, 520, and 530 will be performed as the needle position or orientation is adjusted (560). The user may continue adjusting the position or orientation of the needle 50 until alignment is achieved.

One of skill in the art will understand that components or steps described herein regarding a given embodiment or set of embodiments may readily be omitted, substituted, or added from, with, or to components or steps of other embodiments or sets of embodiments, as appropriate or desirable.

Thus, embodiments of APPARATUS FOR ALIGNING NEEDLE WITH PORT OF INFUSION DEVICE are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A needle apparatus for aligning a needle with a port of an implantable infusion device, the needle apparatus comprising:
   a needle anchoring portion configured to fix the needle apparatus a distance from a distal end of the needle;
   a port locating portion fixable relative to the needle anchoring portion, the port locating portion comprising a port location signal receiver for receiving a signal from the implantable infusion device regarding a location of the port of the implantable infusion device; and
   a processor operably coupled to the port location signal receiver, wherein the processor is configured to determine an orientation of the needle relative to the port based on (i) the signal from the implantable infusion device received by the port location signal receiver, (ii) a distance from an axial center of the needle to the port locating portion, and (iii) a distance along a length of the needle from the distal end of the needle to the port locating portion.

2. The needle apparatus of claim 1, wherein the port locating portion is detachable from the needle anchoring portion.

3. The needle apparatus of claim 1 further comprising the needle.

4. The needle apparatus of claim 1, further comprising a display operably coupled to the processor and configured to provide a user of the apparatus information regarding the orientation of the needle relative to the port based on the signal from the implantable infusion device received by the port location signal receiver.

5. The needle apparatus of claim 4, wherein the port locating portion houses the processor and the display.

6. The needle apparatus of claim 1, wherein the processor is further configured to determine a distance from a tip of the needle to the port of the implantable infusion device.

7. A needle apparatus for aligning a needle with a port of an implantable infusion device, the needle apparatus comprising:
   a needle anchoring portion
      (i) configured to fix the needle apparatus a distance from a distal end of the needle,
      (ii) having a proximal end portion, a distal end portion, and a lumen extending through the needle anchoring portion from the proximal end portion to the distal end portion, and
      (iii) configured such that, when fixed relative to the needle, the lumen of the needle anchoring portion is in fluid communication with a lumen of the needle;
   a port locating portion fixable relative to the needle anchoring portion, the port locating portion comprising a port location signal receiver for receiving a signal from the implantable infusion device regarding a location of the port of the implantable infusion device; and
   a processor operably coupled to the port location signal receiver, wherein the processor is configured to determine an orientation of the needle relative to the port based on the signal from the implantable infusion device received by the port location signal receiver, a distance from an axial center of the needle to the port locating portion, and a distance along a length of the needle from the distal end of the needle to the port locating portion.

8. The needle apparatus of claim 7, wherein the port locating portion is detachable from the needle anchoring portion.

9. The needle apparatus of claim 7, further comprising the needle.

10. The needle apparatus of claim 7, wherein the processor is further configured to determine a distance from a tip of the needle to the port of the implantable infusion device.

11. The needle apparatus of claim 7, further comprising a display operably coupled to the processor and configured to provide a user of the apparatus information regarding the orientation of the needle relative to the port based on the signal from the implantable infusion device received by the port location signal receiver.

12. The needle apparatus of claim 11, wherein the port locating portion houses the processor and the display.

13. A system comprising:
   (a) a needle apparatus for aligning a needle with a port of an implantable infusion device, the needle apparatus comprising:
      (i) a needle anchoring portion configured to fix the needle apparatus a distance from a distal end of the needle; and
      (ii) a port locating portion fixable relative to the needle anchoring portion, the port locating portion comprising a port location signal receiver for receiving a signal from the implantable infusion device regarding a location of the port of the implantable infusion device; and
   (b) a processor operably coupled to the port location signal receiver, wherein the processor is configured to determine an orientation of the needle relative to the port based on (i) the signal from the implantable infusion device received by the port location signal receiver, (ii) a distance from an axial center of the needle to the port locating portion, and (iii) a distance along a length of the needle from the distal end of the needle to the port locating portion.

* * * * *